(12) United States Patent
Orr

(10) Patent No.: US 8,734,502 B2
(45) Date of Patent: May 27, 2014

(54) TAPERED STENT AND FLEXIBLE PROSTHESIS

(75) Inventor: David E. Orr, Central, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 543 days.

(21) Appl. No.: 12/622,739

(22) Filed: Nov. 20, 2009

(65) Prior Publication Data

US 2010/0152835 A1   Jun. 17, 2010

Related U.S. Application Data

(60) Provisional application No. 61/138,435, filed on Dec. 17, 2008.

(51) Int. Cl.
*A61F 2/06* (2013.01)
*A61F 2/07* (2013.01)

(52) U.S. Cl.
CPC .... *A61F 2/06* (2013.01); *A61F 2/07* (2013.01)
USPC .......... 623/1.15; 623/1.13; 623/1.16; 623/1.2

(58) Field of Classification Search
USPC ...................................... 623/1.15, 1.16, 1.37
See application file for complete search history.

(56) References Cited

U.S. PATENT DOCUMENTS

| | | | |
|---|---|---|---|
| 5,836,966 A | 11/1998 | St. Germain | |
| 6,190,406 B1 | 2/2001 | Duerig et al. | |
| 6,273,910 B1 | 8/2001 | Limon | |
| 6,423,084 B1 | 7/2002 | St. Germain | |
| 6,558,425 B2 | 5/2003 | Rockwood, Jr. | |
| 6,569,193 B1 | 5/2003 | Cox et al. | |
| 6,899,729 B1 * | 5/2005 | Cox et al. ..................... | 623/1.13 |
| 7,060,091 B2 | 6/2006 | Killion et al. | |
| 7,279,003 B2 | 10/2007 | Berra et al. | |
| 2002/0052644 A1 | 5/2002 | Shaolian et al. | |
| 2003/0139803 A1 | 7/2003 | Sequin et al. | |
| 2003/0165647 A1 | 9/2003 | Kaneko et al. | |
| 2004/0054403 A1 | 3/2004 | Israel | |
| 2004/0098094 A1 | 5/2004 | Boyle et al. | |

(Continued)

FOREIGN PATENT DOCUMENTS

| | | |
|---|---|---|
| WO | WO 2006/034062 | 3/2006 |
| WO | WO 2006/125382 | 11/2006 |
| WO | WO 2008/051543 | 5/2008 |

OTHER PUBLICATIONS

PCT International Search Report from PCT/US2009/068033 dated Feb. 18, 2010.

(Continued)

*Primary Examiner* — Kathleen Holwerda
*Assistant Examiner* — Sarah W Aleman
(74) *Attorney, Agent, or Firm* — Brinks Gilson & Lione

(57) ABSTRACT

The disclosure relates to a tapered stent and flexible prosthesis. The stent has a first longitudinal region and a second longitudinal region. The second region is substantially parallel to and spaced axially apart from the first region. A plurality of struts is disposed intermediate the first region and the second region and circumferentially connects the first region and the second region. The first region has a longitudinal length that is greater than the second region longitudinal length. The struts have varying longitudinal lengths that gradually decrease from the first region to the second region. The flexible prosthesis comprises at least two alternating tapered stents.

15 Claims, 11 Drawing Sheets

(56) References Cited

U.S. PATENT DOCUMENTS

| | | |
|---|---|---|
| 2004/0102831 A1 | 5/2004 | Murray, III |
| 2004/0106978 A1 | 6/2004 | Greenberg et al. |
| 2004/0158312 A1 | 8/2004 | Chouinard et al. |
| 2005/0137677 A1 | 6/2005 | Rush |
| 2005/0149168 A1* | 7/2005 | Gregorich .................... 623/1.15 |
| 2006/0034883 A1 | 2/2006 | Dang et al. |
| 2006/0178733 A1 | 8/2006 | Pinchuk et al. |
| 2007/0112412 A1 | 5/2007 | Shokoohi et al. |

OTHER PUBLICATIONS

PCT Written Opinion from PCT/US2009/068033 dated Feb. 18, 2010.

* cited by examiner

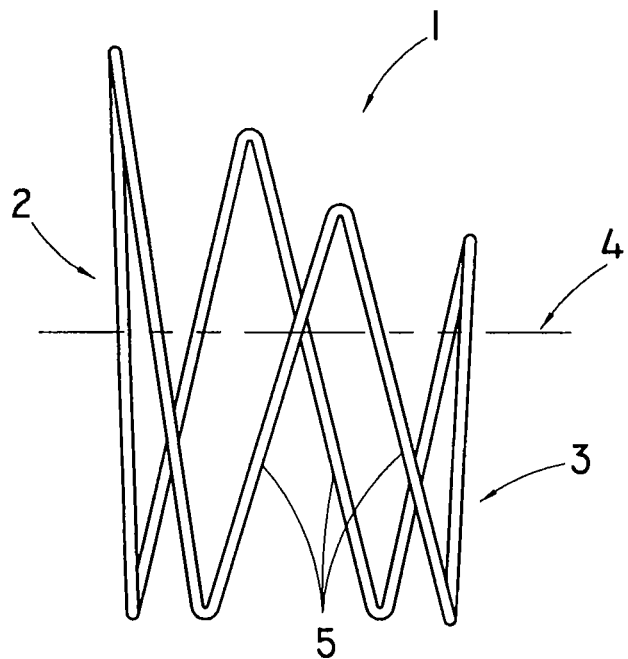
FIG. IA
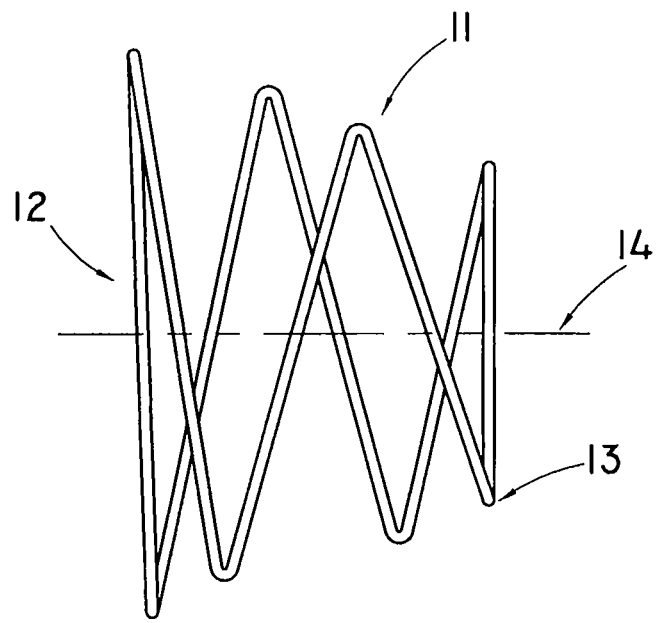
FIG. IB

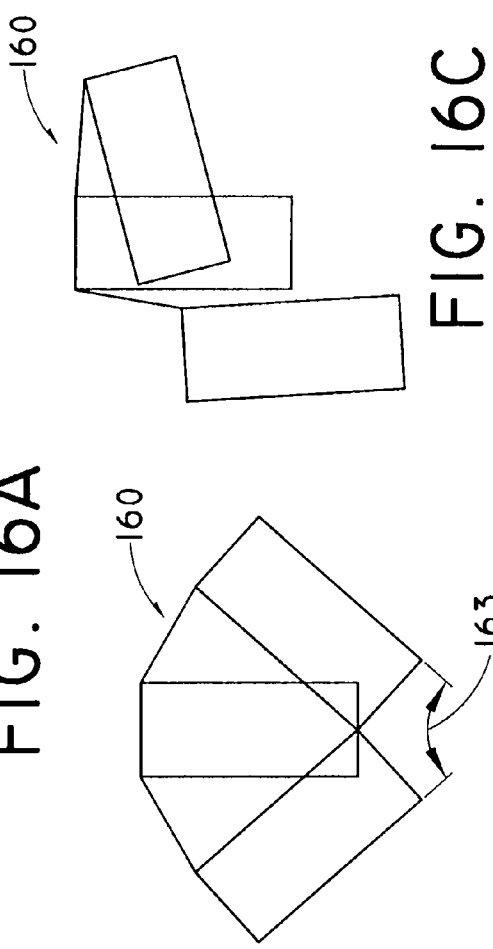
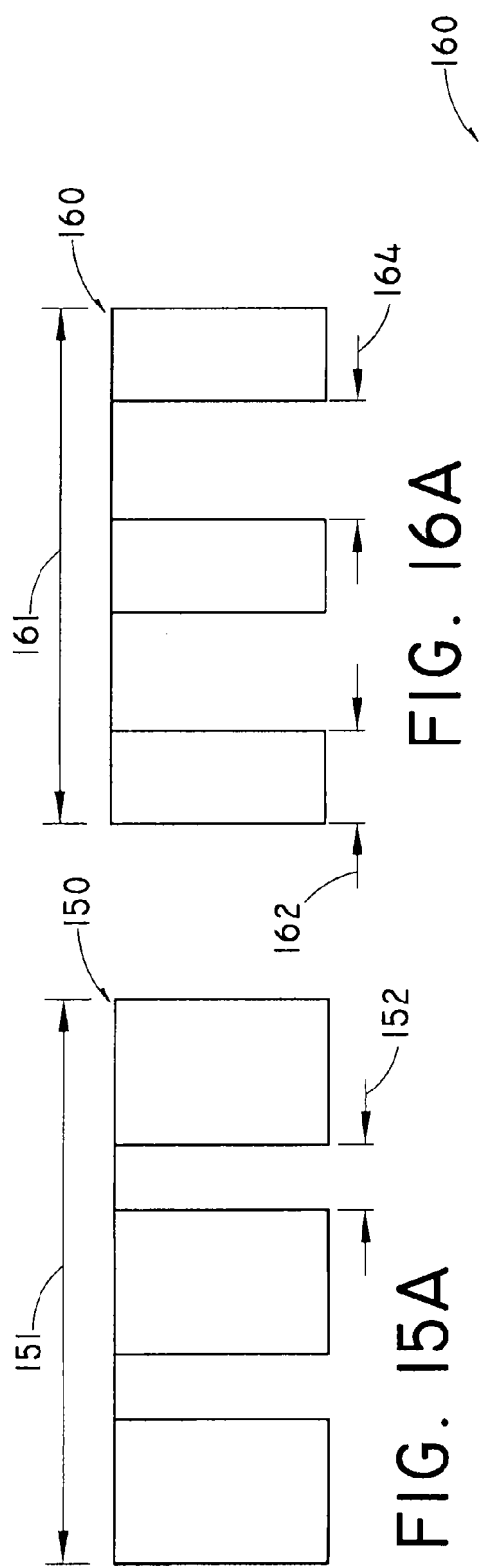
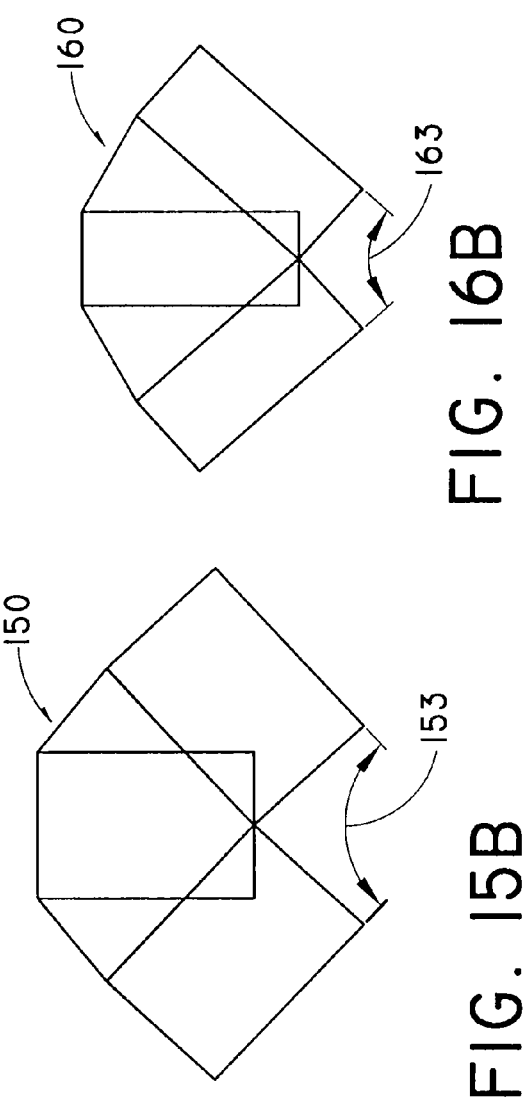

TAPERED STENT AND FLEXIBLE PROSTHESIS

PRIORITY CLAIM

This application claims the benefit of provisional U.S. Patent Application Ser. No. 61/138,435, filed Dec. 17, 2008, which is incorporated herein by reference in its entirety.

BACKGROUND

Aneurysms occur in blood vessels in locations where, due to age, disease or genetic predisposition, insufficient blood vessel strength or resiliency may cause the blood vessel wall to weaken and/or lose its shape as blood flows through it, resulting in a ballooning or stretching of the blood vessel at the limited strength/resiliency location, thus forming an aneurysmal sac. Left untreated, the blood vessel wall may continue to expand to the point where the remaining strength of the blood vessel wall is insufficient and the blood vessel will fail at the aneurysm location, often with fatal result.

To prevent rupture, various implantable prostheses may be introduced into the blood vessel. Minimally invasive methods for implantation of these prostheses have been developed to deliver these prostheses within the lumen of a blood vessel. These prostheses are advantageously inserted intravascularly, such as from an implantation catheter. For example, to prevent rupture of an aneurysm, a tubular stent graft may be introduced into the blood vessel and deployed and secured in a location within the blood vessel such that the stent graft spans the aneurysmal sac. The outer surface of the stent graft, at its opposed ends, abuts and seals against the interior wall of the blood vessel at a location where the blood vessel wall has not suffered a loss of strength or resiliency. U.S. Pat. Nos. 6,423,084 and 7,060,091 disclose stents having varying outward radial force along their length to provide greater force in vessel regions requiring greater force and less force in regions requiring less. The stent graft channels the blood flow through the hollow interior of the stent graft, thereby reducing, if not eliminating, any stress on the blood vessel wall at the aneurysmal sac location.

One particular example of an aneurysm is a thoracic aortic aneurysm. The tortuous and hardened anatomy of a thoracic aortic aneurysm presents several challenges when implanting a prosthesis. Many current prostheses may be limited in their ability to conform to the radial and tortuous curvature, possibly resulting in poor sealing at the proximal and/or distal portion of the prosthesis. Some prostheses designs incorporate features designed to improve the radial curvature and conformability of the prosthesis when used in a directionally constrained fashion. For example, U.S. Patent Application No. 2002/0052644 discloses a prosthesis having a support structure including sliding links to permit flexibility. While the directional constraint may provide improved conformance, the same directional constraint makes the prosthesis more difficult to properly deploy in the thoracic aorta with a possibly increased risk of nonconformance should the directional features not line up with the appropriate radius (inner and outer).

SUMMARY

In a first aspect, a stent for implantation in a body vessel is provided. The stent comprises a circumferential element including a first longitudinal region and a second longitudinal region. The second longitudinal region is substantially parallel to and spaced axially apart from the first region. The first region has a longitudinal length that is greater than the second region longitudinal length. A plurality of struts is disposed intermediate the first region and the second region and circumferentially connects the first region and the second region. The struts comprise varying longitudinal lengths that gradually decrease from the first region to the second region. In one example, the stent may be a Z-stent. In another example, the stent is an asymmetric tube having a continuously decreasing axially length from the first region to the second region.

In another aspect, the stent comprises a circumferential element comprising quadrants. The first and third quadrants are axially opposed to one another. The second and fourth quadrants are axially opposed to one another. The first quadrant may have a longitudinal length about equal to the third quadrant longitudinal length. The second quadrant has a longitudinal length about equal to the fourth quadrant longitudinal length. The first and third quadrant longitudinal lengths are greater than the second and fourth quadrant longitudinal lengths. In one example, a plurality of struts comprising varying longitudinal lengths may circumferentially connect the first, second, third, and fourth quadrants.

In a further aspect, an intraluminal prosthesis comprises a graft having a proximal end, a distal end, and a body defining a lumen extending between the proximal end and the distal end. The body comprises at least a first tapered stent and a second tapered stent. The first and second tapered stents each have a first region aligned along the circumference of the stent and a second region aligned along the circumference of the stent and axially displaced from the first region. The first regions each have a longitudinal length greater than the longitudinal length of the second regions. A plurality of struts is disposed intermediate the first region and the second region and circumferentially connects the first region and the second region. The struts comprise varying longitudinal lengths that gradually decrease from the first region to the second region. In one example, the first region of the first stent is aligned with the second region of the second stent. The stents may be of any configuration. In one example, the stents are Z-stents. In another example, the stent is an asymmetric tube having a continuously decreasing axial length from the first region to the second region.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The stent and stent-graft may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

FIG. 1A is a perspective view of one example of a tapered stent.

FIG. 1B is a perspective view of another example of a tapered stent.

FIGS. 15A-15B schematically depict a radial curvature for another 3-stent conventional stent-graft segment, assuming stent overlap.

FIGS. 16A-16B schematically depict a radial curvature for yet another 3-stent conventional stent-graft segment, assuming stent overlap.

FIG. 16C depicts the instability of the stent-graft segment shown in FIGS. 16A-16B.

DETAILED DESCRIPTION

Figure 2A:
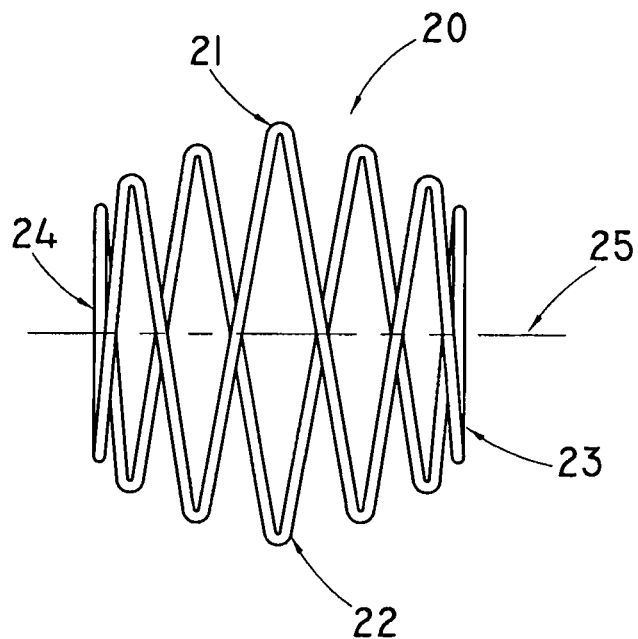
FIG. 2A is a perspective view of a further example of a tapered stent.

The present disclosure provides for a tapered stent and flexible stent-graft for bridging a defect in a body vessel. Exemplary aspects are described below in reference to the stent-grafts application in connection with endovascular treatment of aneurysms and dissections, particularly thoracic aortic aneurysms. However, it is likewise applicable to any suitable endovascular treatment or procedure including, without limitation, endovascular treatment of abdominal aortic aneurysms and dissections.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

"Implantable" refers to an ability of a prosthetic implant to be positioned, for any duration of time, at a location within a body, such as within a body vessel. Furthermore, the terms "implantation" and "implanted" refer to the positioning, for any duration of time, of a prosthetic implant at a location within a body, such as within a body vessel.

"Body vessel" means any body passage lumen that conducts fluid, including but not limited to blood vessels such as those of the human vasculature system, esophageal, intestinal, billiary, urethral and ureteral passages.

"Graft" means a member that acts as an artificial vessel. A graft by itself or with the addition of other elements can be an endoluminal prosthesis.

"Stent" means any device or structure that adds rigidity, expansion force, and/or support to a prosthesis.

"Stent graft" refers to a prosthesis comprising a stent and a graft associated therewith that forms a lumen through at least a portion of its length.

The terms "about" or "substantially" used with reference to a quantity includes variations in the recited quantity that are equivalent to the quantity recited, such as an amount that is insubstantially different from a recited quantity for an intended purpose or function.

"Proximal" means that position or portion of a component which is closest to the patient's heart.

"Distal" means that position of portion of a component which is furthest from the patient's heart.

"Biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

"Extracellular matrix" (ECM) is a collagen-rich substance that is found in between cells in animal tissue and serves as a structural element in tissues. It is generally a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, dura mater, liver basement membrane, pericardium or other tissues.

"Submucosa" refers to a layer of collagen-containing connective tissue occurring under the mucosa in most parts of the alimentary, respiratory, urinary, and genital tracts of animals. A specific example of an ECMM is small intestinal submucosa (SIS), such as is described in U.S. Pat. No. 6,206,931, which is incorporated herein by reference.

Tapered Stent

FIGS. 1A and 1B depict exemplary tapered stents having a taper from one side 2 of the stent to the axially opposing side 3 of the stent. In FIG. 1A, the tapered stent 1 comprises a tapered 4-point Z-stent configuration having an offset taper. The stent comprises struts 5 of varying lengths. The strut 5 length of the stent 1 varies to form a trapezoidal side profile with a long stent length side ($L_L$) 2 and a short stent length side ($L_S$) 3. As shown, the offset taper, as defined herein, is one which originates at the long stent length side 2 and tapers non-symmetrically with the short length side 3 off center with an imaginary centerline 4 drawn perpendicular to and through the midpoint of the long stent length side 2. Although FIG. 1A shows a 4-point Z-stent, the stent may have greater or few points, and need not be a Z-stent.

FIG. 1B depicts a tapered 4-point Z-stent 11 having a mid-line taper. The mid-line taper, as defined herein, is one that originates at the long length side 12 and tapers symmetrically with both the short length side 13 and the long length side 12 centered about an imaginary centerline 14 drawn through each midpoint. The side profile of a mid-line tapered Z-stent would form that of an isosceles trapezoid. Although FIG. 1B shows a 4-point Z-stent, the stent may have greater or few points, and need not be a Z-stent.

Tapered stents are not limited to single taper stents, and may have any suitable tapering configuration. For example, FIG. 2A depicts a tapered 7-point Z-stent 20 comprising a dual mid-line taper with the long stent length at the mid-line and the short stent length at the sides. The stent 20 has a first long length side 21, a second long length side 22, a first short length side 23, and a second short length side 24. The dual mid-line taper originates at the first and second long length sides 21 and 22 and tapers symmetrically with both the both the first and second short length sides 23 and 24 and the first and second long length sides 21 and 22 centered about an imaginary centerline 25 drawn through each midpoint. Viewed from the long length side the stent 20 has a biconvex side profile.

Figure 2B:
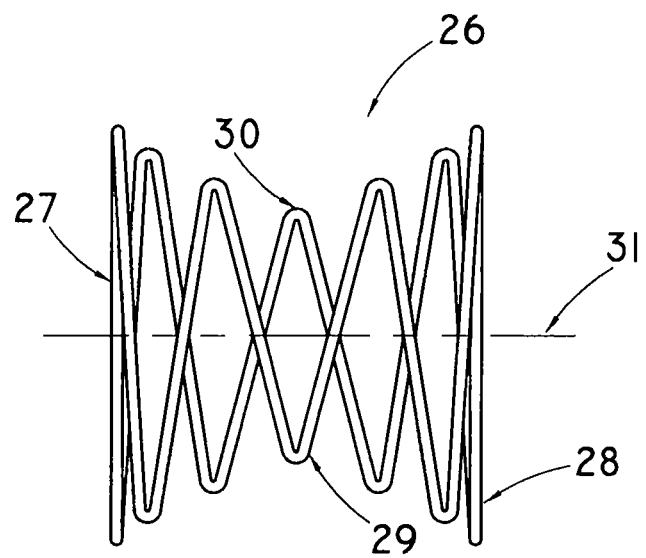
FIG. 2B are perspective views of yet another example of a tapered stent.

FIG. 2B depicts a tapered 7-point Z-stent 26 comprising a dual mid-line taper with the short stent length at the mid-line and the long stent length at the sides. The stent 26 has a first long length side 27, a second long length side 28, a first short length side 29, and a second short length side 30. The dual mid-line taper originates at the first and second short length sides 29 and 30 and tapers symmetrically with both the both the first and second long length sides 27 and 28 and the first and second short length sides 29 and 30 centered about an imaginary centerline 31 drawn through each midpoint. Viewed from the short length side the stent 26 has a biconcave side profile.

The ratio of the long length side to the short length side ($L_L:L_S$) may be any suitable ratio, and the tapered stent need only be able to provide the functionality described herein. The optimal ratio will depend on several factors, including the type of taper and intended use. For example, a specific $L_L:L_S$ may be selected to enhance and maintain stability of a tapered stent. A high $L_L:L_S$ may adversely affect a tapered stent's stability when expanded and deployed in a body vessel. In one example, to enhance stability in a stent having an offset taper, $L_L:L_S$ is between about 1:1 to about 2:1; between about 1.2:1 and about 1.8:1; between about 1.4:1 and about 1.6:1. In a particularly preferred example, $L_L:L_S$ for a stent having an offset taper is no greater than 2:1.

In another example, to enhance the stability of a stent having a midline taper, $L_L:L_S$ is between about 1:1 to about 10:1; between about 1.5:1 and about 5:1; between about 2:1 and about 2.5:1. In a particularly preferred example, $L_L:L_S$ for a stent having a midline taper is no greater than 10:1.

In the expanded configuration, the stents may have a radial force sufficient to maintain the prosthesis at a desired treatment location within a body vessel. Due to the varying stent strut length, a constant strut diameter may result in non-equivalent radial force about the tapered stent circumference. Tapering the strut diameter along the length of the tapered stent may balance the substantially radial force about a tapered stent's circumference. For example, the mechanical properties of the strut diameter and strut length may be used to substantially balance the radial force about a tapered stent circumference in the deployed configuration.

Figure 3:
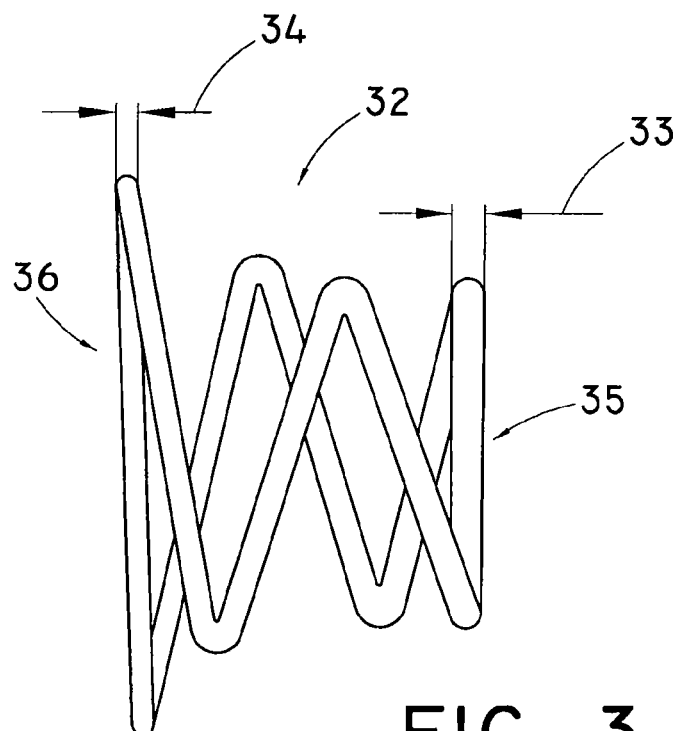
FIG. 3 is a perspective view of an example of a tapered stent having a tapering diameter.
Figure 4:
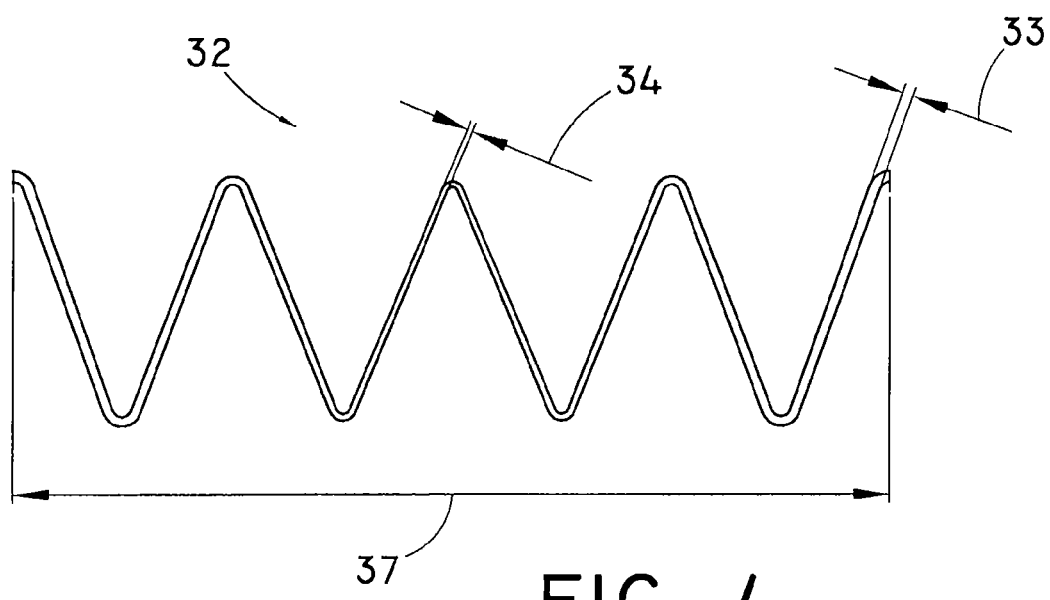
FIG. 4 depicts the tapered stent illustrated in FIG. 3 viewed along the radial plane.

FIG. 3 depicts one example of a tapering stent having a tapering diameter. The mid-line taper stent 32 is made from wire having a tapering diameter. The tapering wire diameter provides for a larger diameter ($D_S$) 33 for the shorter strut lengths 35 and gradually decreases to a smaller diameter ($D_L$) 34 for the longer strut lengths 36. Further depicted in FIG. 4, the short strut length diameter 33 is greater than the long strut length diameter 34 ($D_S > D_L$), thereby providing equivalent radial force about the tapered stent circumference 37.

The tapered aspect of the strut diameter may correlate with the change in strut length. For example, the rate of change in strut diameter per change in strut length ($\Delta D/\Delta L$) may provide equivalent radial force about the stent circumference. In one example, such as the tapered stent of FIG. 4, $\Delta D/\Delta L$ may be linear, thereby producing a constant radial force about the circumference of the stent despite changes in the strut length.

Tapered strut diameter may be manufactured by, for example, modifying the extrusion, or drawing, process through variable extrusion/draw speed or variable extrusion/drawing orifice diameter. In one example, an adjustable drawing die may be set to increase and decrease the die diameter at a constant rate, thereby modifying the strut diameter by a given $\Delta D$ over a given change in length $\Delta L$. For example, an iris configuration may be utilized to create the adjustable diameter drawing die.

In general, stents for use in connection with the present invention, such as stents 1, 11, or otherwise, typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

The stents may be self-expanding or balloon-expandable, and may be deployed according to conventional methodology, such as by an inflatable balloon catheter, by a self-deployment mechanism (after release from a catheter), or by other appropriate means. The stents may be bifurcated, configured for any body vessel including coronary arteries and peripheral arteries (e.g., renal, superficial femoral, carotid, and the like), a urethral stent, a biliary stent, a tracheal stent, a gastrointestinal stent, or an esophageal stent, for example.

The stents may be made of one or more suitable biocompatible materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or nitinol.

Flexible Stent-graft

Figure 5:
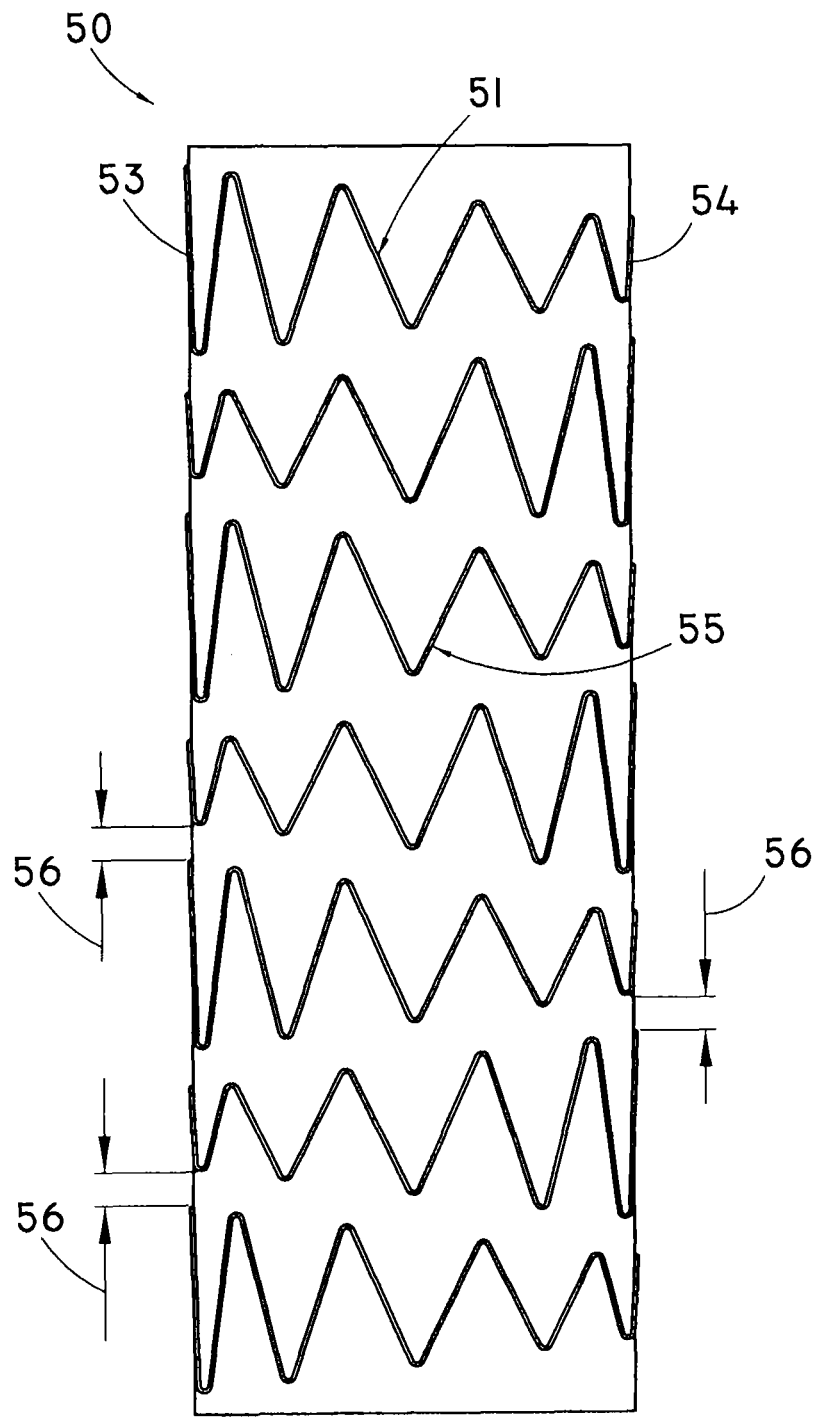
FIG. 5 is a perspective view of one example of a tapered stent-graft.
Figure 6:
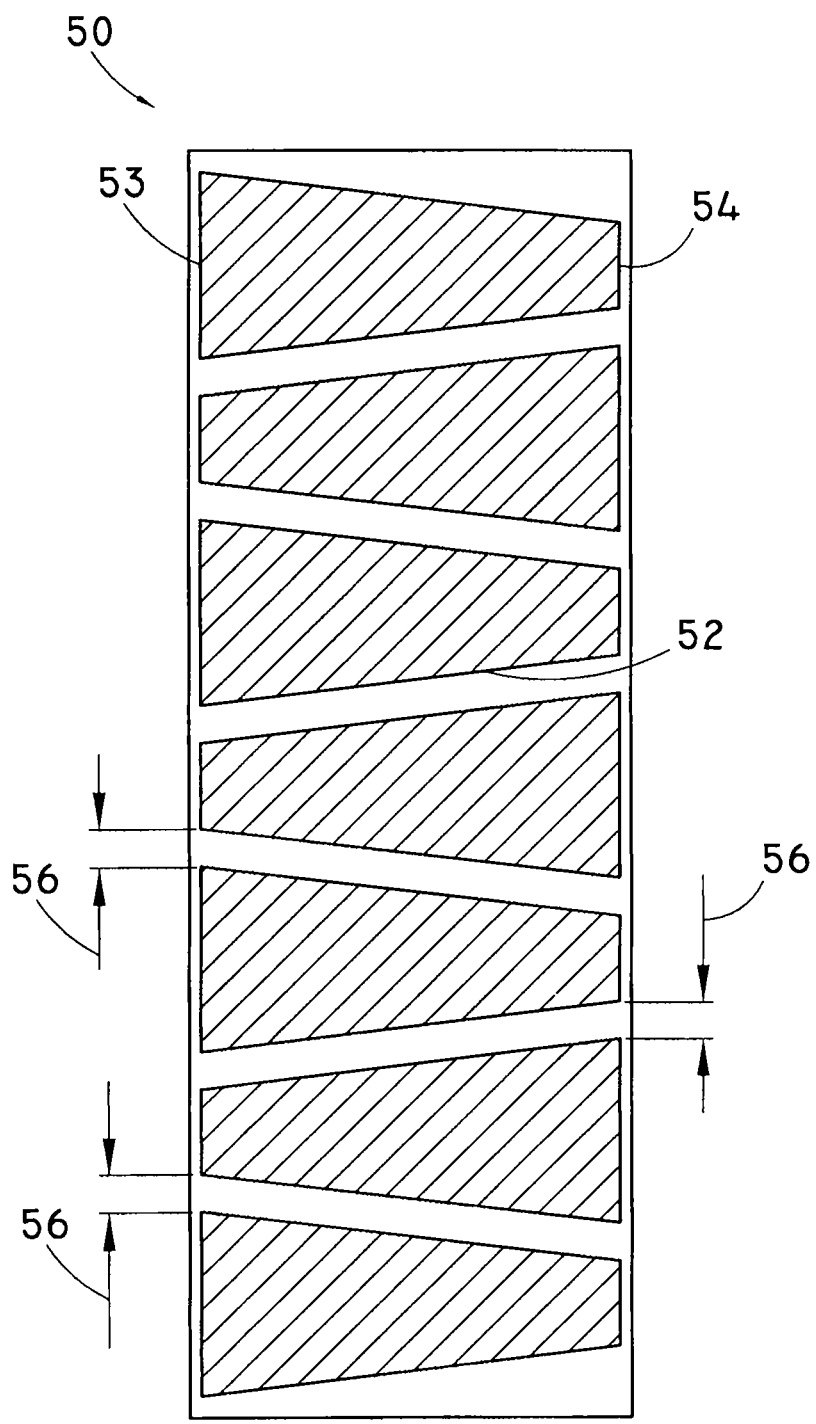
FIG. 6 is a schematic illustration of the tapered stent-graft shown in FIG. 5.

FIG. 5 depicts an exemplary stent-graft having improved flexibility and conformance to tortuous anatomy, such as the thoracic aorta. The stent-graft 50 includes tapered stents 51 positioned in an alternating fashion over the length of the graft 50. The tapered stents 51 create a trapezoid 52 (shown in FIG. 6) when viewed from a side profile with one side consisting of a long strut length $L_L$ 53 and the other side consisting of a short strut length $L_S$ 54 with intermediate struts 55 varying in length according to taper. Alternating short and long strut lengths 54 and 53 provides enhanced flexibility in bending the stent-graft 50 into a radius while providing sufficient stent contact area. Further, the alternating tapered stent configuration provides flexibility that is not directionally constrained or dependent.

In one example, the tapered stents 51 are of similar configuration, permitting equal graft gap spacing 56 at all points between two adjacent stents. Equal graft gap spacing 56, combined with the alternating taper, may provide additional stent-graft flexibility.

It is possible to calculate the radial curvature possible for a stent-graft segment comprising alternative tapered stents. For example, the angles θ and α may define the achievable radial curvature of a stent-graft segment when an opposing tapered stent 70 is rotated until making contact with the imaginary trapezoidal boundary line of an adjacent tapered stent 71. Note that the analysis below does not account for possible overlap of adjacent tapered stents, which may result in even greater angles of stent-graft segment radial curvature.

Figure 7A:
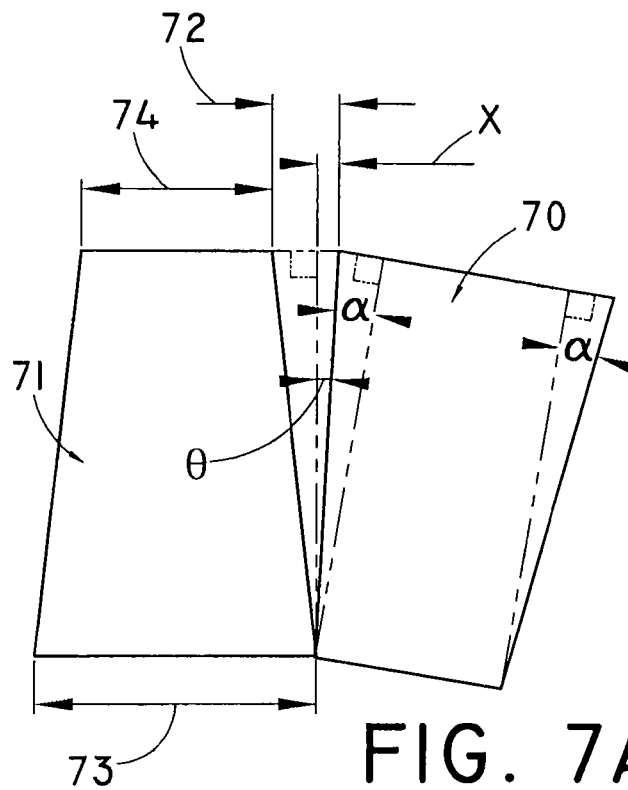
FIGS. 7A and 7B schematically depict the radial curvature possible for a tapered stent-graft segment comprising alternating tapered stents.

As depicted in FIG. 7A, where the graft gap spacing 72 Is less than or equal to the long length side 73 minus the short length side 74 (e.g., Graft Gap Spacing≤[$L_L$−$L_S$]):

$$\text{If } X \leq \left(\frac{L_L - L_S}{2}\right)$$

$$\Theta = \tan^{-1}\left[\frac{\left(GraftGap - \left(\frac{L_L - L_S}{2}\right)\right)}{StentDiameter}\right]$$

$$\alpha = \tan^{-1}\left[\frac{\left(\frac{L_L - L_S}{2}\right)}{StentDiameter}\right]$$

Figure 7B:
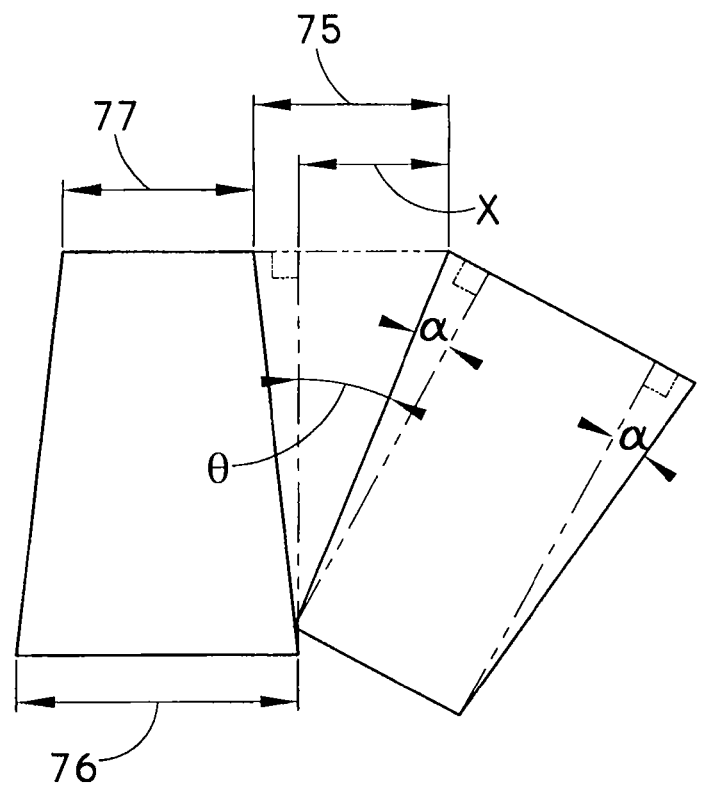

As depicted in FIG. 7B, where the graft gap spacing 75 Is greater than the long length side 76 minus the short length side 77 (e.g., Graft Gap Spacing>[$L_L$−$L_S$]):

$$\text{If } X > \left(\frac{L_L - L_S}{2}\right)$$

$$\Theta = \sin^{-1}\left[\frac{\left(GraftGap - \left(\frac{L_L - L_S}{2}\right)\right)}{\sqrt{\left(\frac{L_L - L_S}{2}\right)^2 + (StentDiameter)^2}}\right]$$

-continued $$\alpha = \tan^{-1}\left[\frac{\left(\frac{L_L - L_S}{2}\right)}{StentDiameter}\right]$$

Figure 8A:
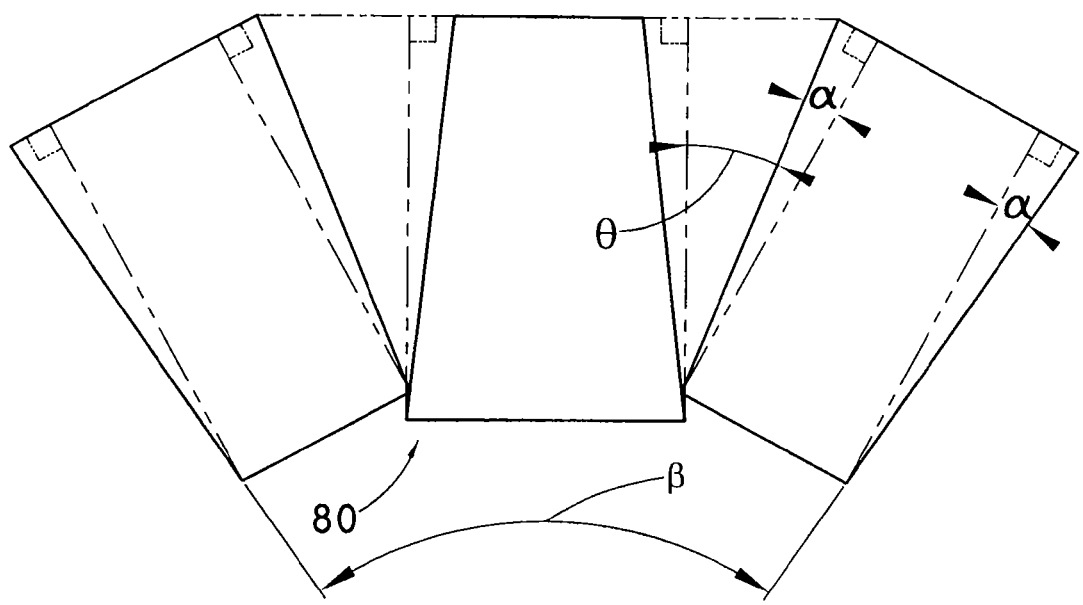
FIG. 8A schematically depicts the radial curvature possible for a 3-tapered stent-graft segment comprising alternating tapered stents.

The total radial curvature for a stent-graft segment including tapered stents may be calculated using the angles θ and α. As noted above, the analysis does not account for possible overlap of adjacent tapered stents, which may result in even greater angles of stent-graft segment radial curvature. For example, the total radial curvature β for a 3-tapered sent-graft segment 80 (shown in FIG. 8A):

β=2(θ+2α)

Figure 8B:
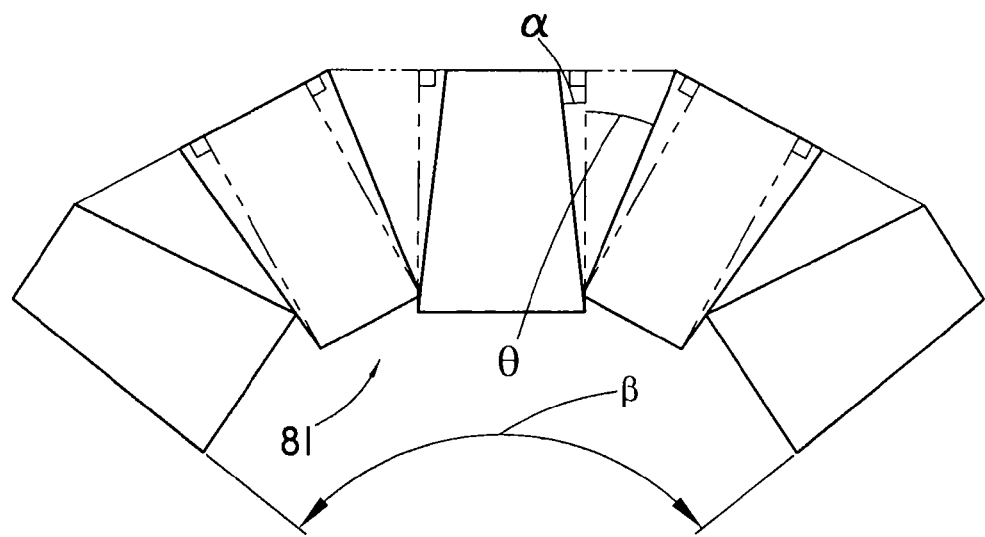
FIG. 8B schematically depicts the radial curvature possible for a 5-tapered stent-graft segment comprising alternating tapered stents.

The total radial curvature β for a 5-tapered sent-graft segment 81 (shown in FIG. 8B):

β=2(2θ+3α)

Figure 9A:
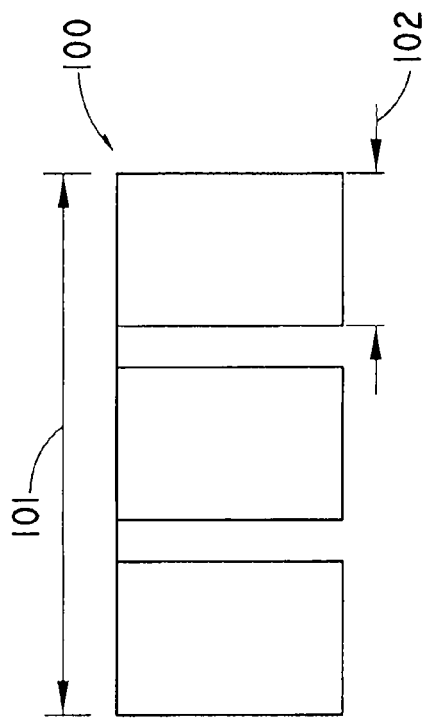
FIGS. 9A-9B schematically depict a radial curvature for a 3-tapered stent-graft segment comprising alternating tapered stents, assuming no stent overlap.
Figure 9B:
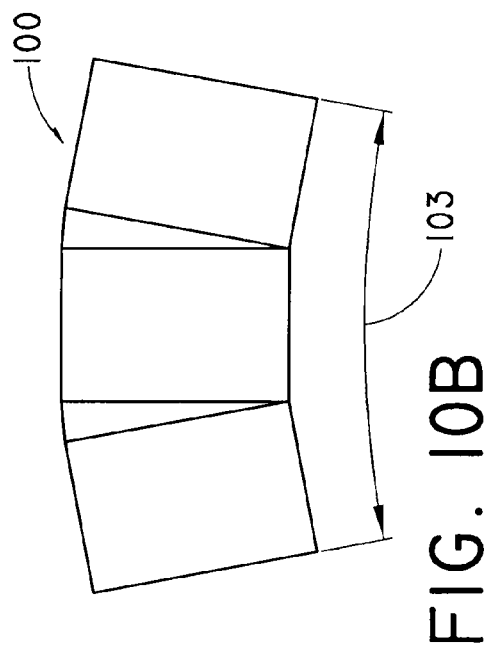

Improved tapered stent-graft flexibility is depicted in FIGS. 9A-9B compared to traditional non-tapered stent-grafts depicted in FIGS. 10A-12B. In the examples depicted in FIGS. 9A-12B, a radial curvature is provided for each stent-graft segment. The radial curvature is intended to be illustrative only and not limit the present disclosure. The curvature is dependent on a number of variables, including the long length side $L_L$, the short length side $L_S$, and the graft gap for each segment. The radial curvature provided for each figure does not limit the wide range of curvatures possible for stent-graft segments.

FIGS. 9A-9B depict the radial curvature for a 3-tapered stent-graft segment 90 having a segment length 91 and alternating stent long length side 92 and short length side 93. The radial curvature achievable 94 is approximately 68 degrees, assuming no stent overlap.

Figure 10A:
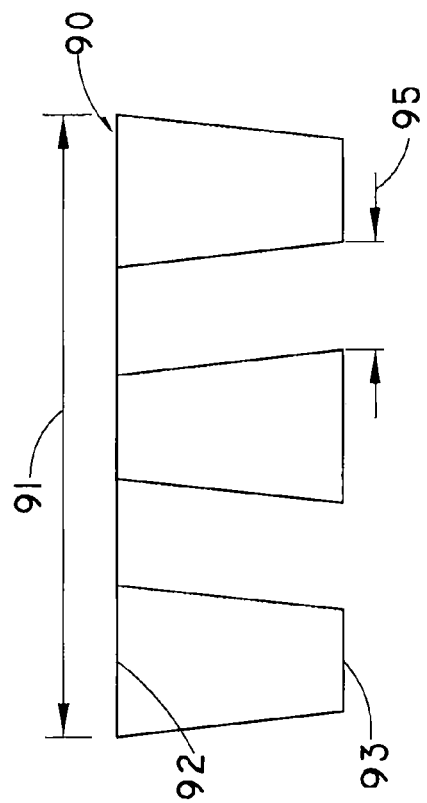
FIGS. 10A-10B schematically depict a radial curvature for a 3-stent conventional stent-graft segment, assuming no stent overlap.
Figure 10B:
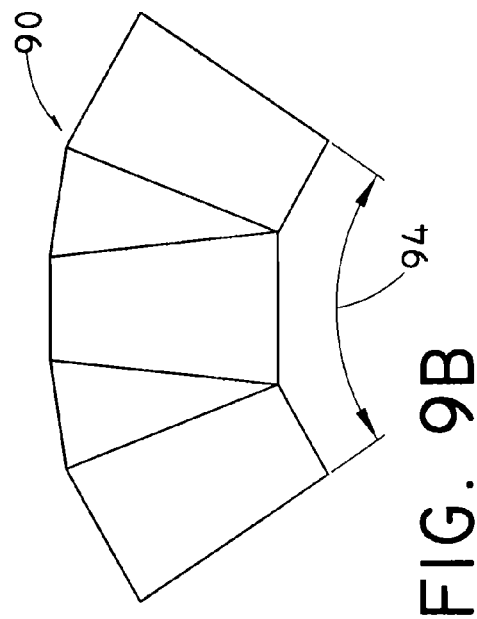

A traditional non-tapered stent-graft 100 is shown in FIGS. 10A-10B. The non-tapered stent-graft segment 100 has a segment length 101 equal to the segment length 91 of the tapered stent-graft segment 90 of FIG. 9A, and a stent length 102 equal to the long length side 92 of FIG. 9A. The traditional non-tapered stent-graft segment 100 only has an achievable radial curvature 103 of about 23 degrees assuming no stent overlap, a decrease of about 45 degrees compared to the tapered stent-graft 90 of FIG. 9B.

Figure 11A:
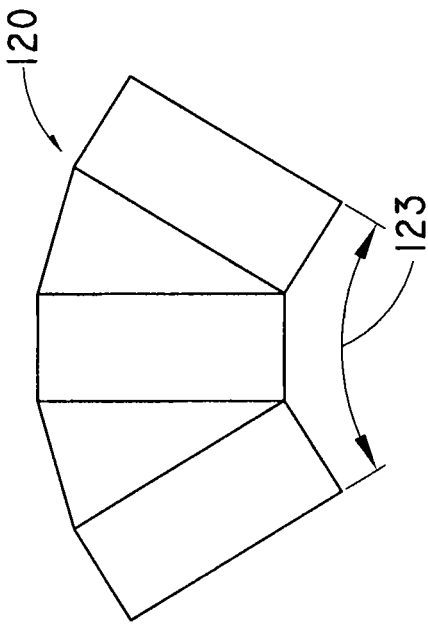
FIGS. 11A-11B schematically depict a radial curvature for another 3-stent conventional stent-graft segment, assuming no stent overlap.
Figure 11B:
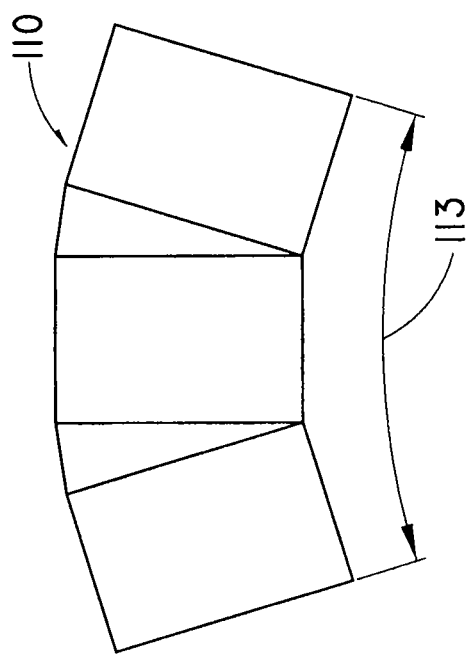

An additional traditional non-tapered stent-graft 110 is shown in FIGS. 11A-11B. The non-tapered stent-graft segment 110 has a segment length 111 equal to the segment length 91 of the tapered stent-graft segment 90 of FIG. 9A, and a graft gap between stents 112 equal to graft gap 95 of FIG. 9A. The traditional non-tapered stent-graft segment 110 only has an achievable radial curvature 113 of about 46 degrees assuming no stent overlap, a decrease of about 22 degrees compared to the tapered stent-graft 90 of FIG. 9B.

Figure 12A:
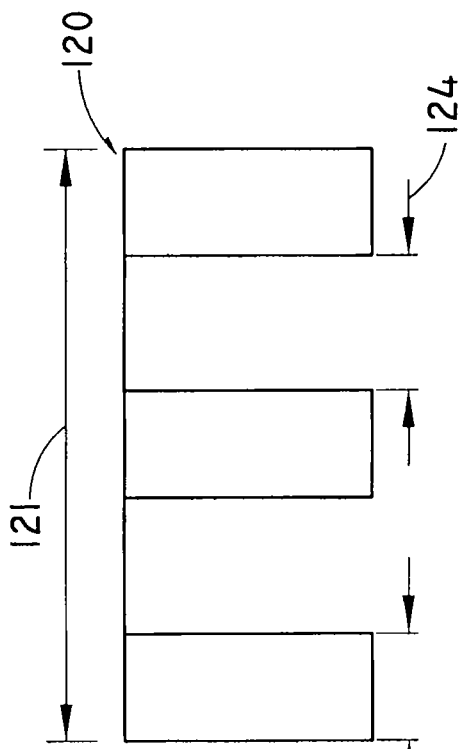
FIGS. 12A-12B schematically depict a radial curvature for yet another 3-stent conventional stent-graft segment, assuming no stent overlap.
Figure 12B:
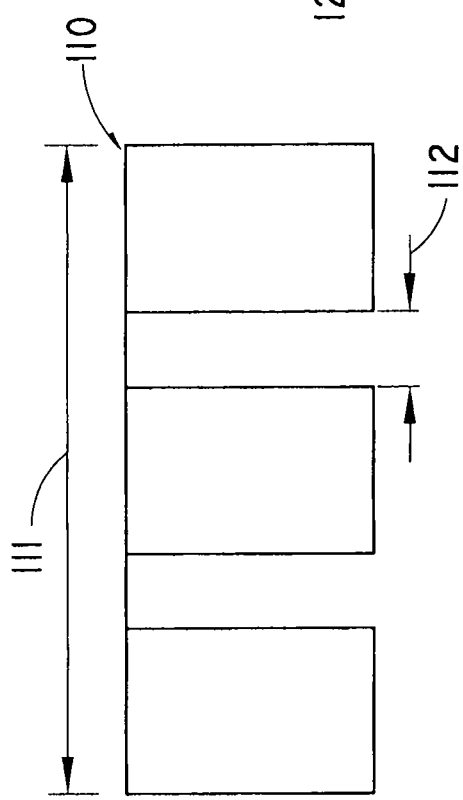

A further traditional non-tapered stent-graft 120 is shown in FIGS. 12A-12B. The non-tapered stent-graft segment 120 has a segment length 121 equal to the segment length 91 of the tapered stent-graft segment 90 of FIG. 9A, and a stent length 122 equal to the short length side 93 of FIG. 9A. The traditional non-tapered stent-graft segment 120 has an achievable radial curvature 123 of about 94 degrees assuming no stent overlap, an increase of about 26 degrees compared to the tapered stent-graft 90 of FIG. 9B. However, the non-tapered stent configuration may exhibit instability due to the short stent lengths 122 and long graft gap 124 necessary to cover the same segment length 121 as the segment length 91 of the tapered stent-graft 90 depicted in FIG. 9A. This results in instability of the stent-graft segment 120, described in further detail below (see FIG. 16C).

FIGS. 13A-16B depict the achievable radial curvature for stent-graft segments having stent overlap. When the stent configurations are allowed to overlap, the enhanced flexing and bending capabilities of the alternating tapered stent-graft configuration are more apparent, as well as improved stability compared to traditional non-tapered stent graft segments.

Figure 13A:
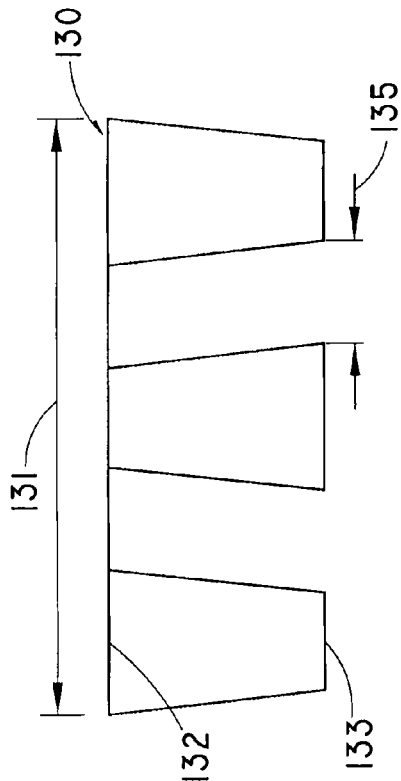
FIGS. 13A-13B schematically depict a radial curvature for a 3-tapered stent-graft segment comprising alternating tapered stents, assuming stent overlap.
Figure 13B:
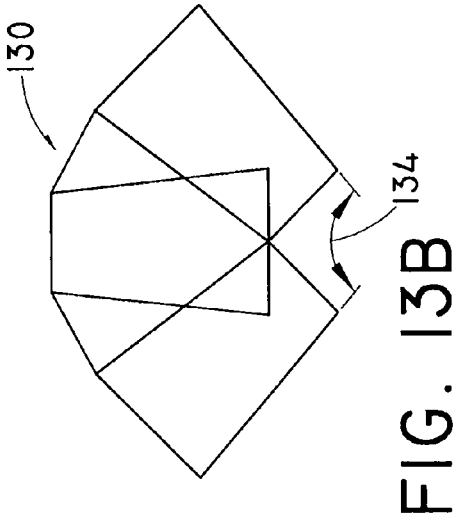

FIGS. 13A-13B depict the radial curvature for a 3-tapered stent-graft segment 130 having a segment length 131 and alternating stent long length side 132 and short length side 133. The radial curvature achievable 134 with stent overlap is approximately 113 degrees.

Figure 14A:
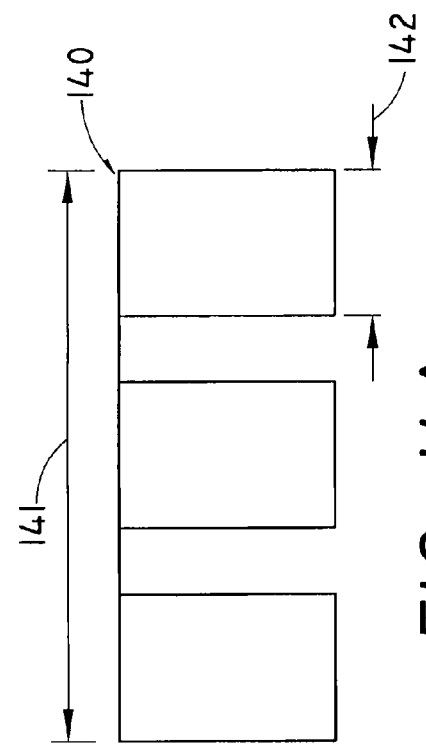
FIGS. 14A-14B schematically depict a radial curvature for a 3-stent conventional stent-graft segment, assuming stent overlap.
Figure 14B:
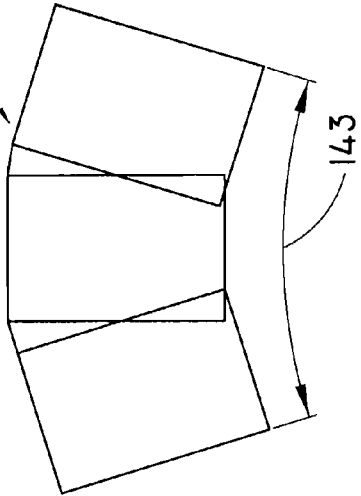

A traditional non-tapered stent-graft 140 is shown in FIGS. 14A-14B. The non-tapered stent-graft segment 140 has a segment length 141 equal to the segment length 131 of the tapered stent-graft segment 130 of FIG. 13A, and a stent length 142 equal to the long length side 132 of FIG. 13A. The traditional non-tapered stent-graft segment 140 only has an achievable radial curvature 143 of about 45 degrees with stent overlap, a decrease of about 68 degrees compared to the tapered stent-graft 130 of FIG. 13B.

An additional traditional non-tapered stent-graft 150 is shown in FIGS. 15A-15B. The non-tapered stent-graft segment 150 has a segment length 151 equal to the segment length 131 of the tapered stent-graft segment 130 of FIG. 13A, and a graft gap between stents 152 equal to graft gap 135 of FIG. 13A. The traditional non-tapered stent-graft segment 150 only has an achievable radial curvature 153 of about 81 degrees with stent overlap, a decrease of about 32 degrees compared to the tapered stent-graft 130 of FIG. 13B.

A further traditional non-tapered stent-graft 160 is shown in FIGS. 16A-16B. The non-tapered stent-graft segment 160 has a segment length 161 equal to the segment length 131 of the tapered stent-graft segment 130 of FIG. 13A, and a stent length 162 equal to the short length side 133 of FIG. 13A. The traditional non-tapered stent-graft segment 160 has an achievable radial curvature 163 of about 116 degrees with stent overlap, an increase of only about 3 degrees compared to the tapered stent-graft 130 of FIG. 13B. However, the non-tapered stent configuration 160 exhibits instability due to the short stent lengths 162 and long graft gap 164 necessary to cover the same segment length 161 as the segment length 131 of the tapered stent-graft 130 depicted in FIG. 13A. This results in instability of the stent-graft segment 160, as depicted in FIG. 16C.

Graft Material

The graft may include any biocompatible material which is suitable for facilitating repair to the injured or diseased body vessel. The graft material may be synthetic, naturally-derived material, and/or manufactured.

For example, graft material may include a film, a coating, a sheet of biocompatible fabrics, non-woven materials or porous materials. Examples of biocompatible polymers from which a graft can be formed include polyesters, such as poly (ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include polymerization of biocompatible polymers from the material surface, coating of the surface with a crosslinked biocompatible polymer, and chemical modification with biocompatible functional groups. Thus, any polymer that may be formed into a porous sheet can be used to make a flexible covering, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above.

In one aspect, the graft material may comprise a biocompatible polyurethane, for example THORALON (THORATEC, Pleasanton, Calif.). As described in U.S. Patent Application Publication No. 2002/0065552 A1, incorporated herein by reference, THORALON is a polyetherurethane urea blended with a siloxane-containing surface modifying additive. THORALON has been used in certain vascular applications and is characterized by thromboresistance, high tensile strength, low water absorption, low critical surface tension and good flex life. A variety of other biocompatible polyurethanes/polycarbamates and urea linkages (hereinafter "—C(O)N or CON type polymers") may also be employed. Biocompatible CON type polymers modified with cationic, anionic and aliphatic side chains may also be used. See, for example, U.S. Pat. No. 5,017,664, which is incorporated herein by reference in its entirety. Other biocompatible CON type polymers include: segmented polyurethanes, such as BIOSPAN; polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PURSIL-10, -20, and -40 TSPU; PTMO and PDMS polyether-based aliphatic siloxane-polyurethanes, such as PURSIL AL-5 and AL-10 TSPU; aliphatic, hydroxy-terminated polycarbonate and PDMS polycarbonate-based siloxane-polyurethanes, such as CARBOSIL-10,-20, and -40 TSPU (all available from POLYMER TECHNOLOGY GROUP). Examples of siloxane-polyurethanes are disclosed in U.S. Pat. Application Publication No. 2002/0187288 A1, which is incorporated herein by reference in its entirety.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference in its entirety.

Examples of biocompatible polyesters include DACRON® (DUPONT, Wilmington, Del.) and TWILL-WEAVE® MICREL (VASCUTEK, Renfrewshire, Scotland).

Another potential biocompatible graft material is ECMM, such as a purified collagen-based matrix derived from submucosa tissue. Upon implantation into a host, ECMM may undergo remodeling and induce the growth of endogenous tissues. When implanted, ECMM may be able to serve as a matrix for, promote and/or induce the growth of endogenous tissue and undergo a process of bioremodeling. Common events related to this bioremodeling process may include: widespread and rapid neovascularization, proliferation of granulation mesenchymal cells, biodegradation/resorption of implanted purified intestinal submucosa material, and lack of immune rejection.

Studies have shown that warm-blooded vertebrate submucosa may be capable of inducing host tissue proliferation, bioremodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization may be observed and the submucosa material may be bioremodeled into host replacement tissue with site-specific structural and functional properties. This may occur as a result of one or more of the components of submucosa including, for example, glycosaminoglycans, glycoproteins, proteoglycans, and/or growth factors, including Transforming Growth Factor-[alpha], Transforming Growth Factor-[beta], and/or Fibroblast Growth Factor 2 (basic).

ECMM is preferably obtained from human or other mammalian sources, including animals raised for meat production, e.g., pigs, cattle and sheep or other warm-blooded vertebrates. More specifically, ECMM is preferably made from a submucosa isolated from the alimentary, respiratory, urinary or genital tracts, renal capsule or other appropriate sources. In general, purified submucosa is prepared from these tissue sources by determinating the purified submucosa from both the smooth muscle layers and the mucosal layers. The preparation of intestinal submucosa is described in U.S. Pat. No. 4,902,508, and the preparation of tela submucosa is described in U.S. patent application Ser. No. 08/916,490, both of which are incorporated herein by reference. The preparation of submucosa is also described in U.S. Pat. No. 5,733,337 and in 17 Nature Biotechnology 1083 (November 1999); and WIPO Publication WO 98/221 58, dated 28 May 1998, which is the published application of PCT/US97/14855.

Purified tela submucosa, a preferred type of ECMM, has been previously described in U.S. Pat. Nos. 6,206,931, 6,358, 284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference.

In a further example, the grafts may comprise a porous biocompatible polymer in which a collagenous biomaterial has been dispersed, as is disclosed in U.S. Provisional Application Ser. No. 60/558,794 filed Mar. 31, 2004 and U.S. Provisional Application Ser. No. 60/558,667 filed Mar. 31, 2004, which are hereby incorporated herein by reference.

The grafts may be made of a single material, or may be a blend, weave, laminate or composite of two or more materials. The graft material may also include other additives, such as plasticizers, compatibilizers, surface modifiers, biological materials such as peptides and enzymes, and therapeutic agents such as drugs or other medicaments.

In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

In one example, to achieve enhanced collapsibility, the material from which the graft is produced may be selected based on the material's ability to achieve an enhanced collapsibility.

Delivery of Stent Graft

Stent grafts can be configured for delivery to a body vessel. For example, a prosthesis comprising tapered stents according to the present disclosure can be compressed to a delivery configuration within a retaining sheath that is part of a delivery system, such as a catheter-based system. Upon delivery, the prosthesis can be expanded, for example, by inflating a balloon from inside the stents. The delivery configuration can be maintained prior to deployment of the prosthesis by any suitable means, including a sheath, a suture, a tube or other restraining material around all or part of the compressed prosthesis, or other methods.

Prostheses can be deployed in a body vessel by means appropriate to their design. Prostheses of the present disclosure can be adapted for deployment using conventional methods known in the art and employing percutaneous transluminal catheter devices. The prostheses are designed for deployment by any of a variety of in situ expansion means.

In one example, a prosthesis comprising self-expanding tapered stents of the present disclosure may be mounted onto a catheter that holds the prosthesis as it is delivered through the body lumen and then releases the prosthesis and allows it to self-expand into contact with the body lumen. This deployment is effected after the prosthesis has been introduced percutaneously, transported transluminally and positioned at a desired location by means of the catheter. The self-expanding prosthesis may be deployed according to well-known deployment techniques for self-expanding medical devices. For example, the prosthesis may be positioned at the distal end of a catheter with a removable sheath or sleeve placed over the prosthetic valve to hold the prosthesis in a contracted state with a relatively small diameter. The prosthesis may then be implanted at the point of treatment by advancing the catheter over a guide wire to the location of the lesion and then withdrawing the sleeve from over the prosthesis. The stent graft will automatically expand and exert pressure on the wall of the blood vessel at the site of treatment. The catheter, sleeve, and guide wire are removed from the patient.

In some examples, a bioabsorbable suture or sheath can be used to maintain a self-expanding stent graft in a compressed configuration both prior to and after deployment. As the bioabsorbable sheath or suture is degraded by the body after deployment, the prosthesis can expand within the body vessel. In some examples, a portion of the prosthesis can be restrained with a bioabsorbable material and another portion allowed to expand immediately upon implantation. For example, a self-expanding stent graft can be partially restrained by a bioabsorbable material upon deployment and later expand as the bioabsorbable material is absorbed.

In another example, a stent graft may be first positioned to surround a portion of an inflatable balloon catheter. The prosthesis, with the balloon catheter inside is configured at a first, collapsed diameter. The prosthesis and the inflatable balloon are percutaneously introduced into a body vessel, following a previously positioned guide wire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthesis are positioned within the body passageway at the point where the prosthesis is to be placed. Thereafter, the balloon is inflated and the prosthesis is expanded by the balloon portion from the collapsed diameter to a second expanded diameter. After the prosthesis has been expanded to the desired final expanded diameter, the balloon is deflated, reduced yarn density regions are perforated, and the catheter may be withdrawn, leaving the prosthesis in place. The prosthesis may be covered by a removable sheath during delivery to protect both the prosthesis and the vessels.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

I claim:

1. A stent for implantation in a body vessel, the stent graft comprising:
    a self-expanding circumferential element comprising a first longitudinal region and a second longitudinal region, each region comprising struts,
    the second region being substantially parallel to and spaced across from the first region;
    the first region having struts having a longitudinal length greater than the struts of the second region;
    a plurality of struts disposed between the first region and the second region and circumferentially connects the first region and the second region;
    the struts disposed between the first region and the second region comprising varying longitudinal lengths that gradually decrease from the first region to the second region;
    wherein the struts of the first region and second region each comprise a diameter with the first region diameter less than the second region diameter; and
    where the diameters of the struts decrease from the second region diameter to the first region diameter, as the lengths of the struts increase, and where the rate of change in strut diameter per change in strut longitudinal length is substantially linear, such that the circumferential element produces a substantially constant outward radial force about the element circumference.

2. The stent of claim 1, where the first region has a radial centerline and the strut longitudinal lengths decrease symmetrically about the radial centerline such that second region longitudinal midpoint is aligned with the radial centerline.

3. The stent of claim 2, where the ratio of the first region longitudinal length to the second region longitudinal length is between about 1:1 to about 10:1.

4. The stent of claim 1, where the first region has a radial centerline and the strut longitudinal lengths decrease non-symmetrically about the radial centerline such that the second region is longitudinally offset from the first region.

5. The stent of claim 4, where the ratio of the first region longitudinal length to the second region longitudinal length is between about 1:1 to about 2:1.

6. The stent of claim 1, where the circumferential element is moveable between a first radially compressed configuration and a second radially compressed configuration sized for vessel implantation.

7. The stent of claim 6, where the expanded configuration comprises a Z-shaped zigzag pattern.

8. The stent of claim 1, where the circumferential element comprises a material selected from the group consisting of stainless steel, nitinol, tantalum, a nonmagnetic nickel-cobalt-chromium-molybdenum alloy, platinum, titanium, a suitable biocompatible alloy, a suitable biocompatible material, and a combination thereof.

9. The stent of claim 8, wherein the circumferential element material is nitinol or stainless steel.

10. An intraluminal prosthesis comprising:
    a graft comprising a proximal end, a distal end, and a body defining a lumen extending between the proximal end and the distal end;
    the body comprising at least a first tapered stent and a second tapered stent; the first and second tapered stents each comprising a first longitudinal region and a second longitudinal region, the second region of the first tapered stent being substantially parallel to and spaced across from the first region, and the second region of the second tapered stents being substantially parallel to and spaced across from the first region of the second tapered stent,
    the first region of the first tapered stent having a longitudinal length greater than the longitudinal length of the second region of the first tapered stent, and the first region of the second tapered stent having a longitudinal length greater than the longitudinal length of the second region of the second tapered stent,
    each of the first and second tapered stents further comprising a plurality of struts disposed intermediate their first and second regions that circumferentially connect the first regions and the second regions, the struts comprising varying longitudinal lengths that gradually decrease from the first regions to the second regions;
    where the first stent first region is longitudinally aligned with the second stent second region;
    wherein the struts of the first region of the first tapered stent each comprise a diameter with the first region diameter less than the second region diameter, and wherein the struts of the first region of the second tapered stent each comprise a diameter with the first region diameter less than the second region diameter; and
    where, in each of the first and second tapered stents, the diameters of the struts decrease from the second region diameter to the first region diameter, as the lengths of the struts increase, and where the rate of change in strut diameter per change in strut longitudinal length is substantially linear, such that the circumferential element produces a substantially constant outward radial force about the element circumference.

11. The prosthesis of claim 10, the body further comprising a third tapered stent comprising a first longitudinal region and a second longitudinal region, the second region being substantially parallel to and spaced across from the first region, the first region having a longitudinal length greater than the second region longitudinal length, a plurality of struts disposed intermediate the first region and the second region and circumferentially connecting the first region and the second region, the struts comprising varying longitudinal lengths that gradually decrease from the first region to the second region;
    where the first stent first region is longitudinally aligned with the second stent second region and the third stent first region; and
    where the first stent second region is longitudinally aligned with the second stent first region and the third stent second region.

12. The prosthesis of claim 11, where the longitudinal distance along the body between the first stent and second stent is substantially equal to the longitudinal distance along the body between the second stent and third stent.

13. The prosthesis of claim 10, where the first stent first region has a radial centerline and the first stent strut longitudinal lengths decrease symmetrically about the first stent radial centerline such that first stent second region longitudinal midpoint is aligned with the first stent radial centerline; and where the second stent first region has a radial centerline and the second stent strut longitudinal lengths decrease symmetrically about the second stent radial centerline such that second stent second region longitudinal midpoint is aligned with the second stent radial centerline.

14. The prosthesis of claim 10, where the prosthesis is moveable between a first radially compressed configuration and a second radially compressed configuration sized for vessel implantation.

15. The prosthesis of claim 10, where in the expanded configuration the first stent and second stent each comprise a Z-shaped zigzag pattern.

* * * * *

UNITED STATES PATENT AND TRADEMARK OFFICE
CERTIFICATE OF CORRECTION

PATENT NO. : 8,734,502 B2
APPLICATION NO. : 12/622739
DATED : May 27, 2014
INVENTOR(S) : David E. Orr Page 1 of 1

It is certified that error appears in the above-identified patent and that said Letters Patent is hereby corrected as shown below:

In the Specification

In column 8, about line 12, after "3-tapered" replace "sent-graft" with --stent-graft--.

In column 8, about line 15, after "5-tapered" replace "sent-graft" with --stent-graft--.

Signed and Sealed this
Ninth Day of September, 2014

Michelle K. Lee
*Deputy Director of the United States Patent and Trademark Office*